United States Patent
Horn et al.

(10) Patent No.: US 10,160,701 B2
(45) Date of Patent: Dec. 25, 2018

(54) PROCESSES FOR THE RECOVERY OF AROMATIC HYDROCARBONS FROM VAPOR GAS STREAMS

(71) Applicant: UOP LLC, Des Plaines, IL (US)

(72) Inventors: Ian G. Horn, Streamwood, IL (US); Jason T. Corradi, Arlington Heights, IL (US); Lawrence E. Sullivan, Mount Prospect, IL (US)

(73) Assignee: UOP LLC, Des Plaines, IL (US)

(*) Notice: Subject to any disclaimer, the term of this patent is extended or adjusted under 35 U.S.C. 154(b) by 621 days.

(21) Appl. No.: 14/568,397

(22) Filed: Dec. 12, 2014

(65) Prior Publication Data

US 2016/0168056 A1 Jun. 16, 2016

(51) Int. Cl.
- *C07C 7/00* (2006.01)
- *C07C 7/08* (2006.01)
- *C07C 7/11* (2006.01)

(52) U.S. Cl.
CPC .................................... *C07C 7/11* (2013.01)

(58) Field of Classification Search
CPC B01D 53/14; B01D 53/1475; B01D 53/1456; B01D 53/1425; B01D 53/1406; B01D 53/1412; B01D 53/1418; B01D 53/1431; B01D 53/1487; B01D 53/1493; B01D 2252/103; B01D 2252/205; B01D 2252/2056; C07C 7/11; C07C 15/00
See application file for complete search history.

(56) References Cited

U.S. PATENT DOCUMENTS

| | | | |
|---|---|---|---|
| RE22,379 E | 9/1943 | Dunn et al. | |
| 2,415,192 A | 2/1947 | Rittenhouse | |
| 2,747,000 A | 5/1956 | Nelson | |
| 3,146,190 A | 8/1964 | Papadopoulos et al. | |
| 3,207,692 A * | 9/1965 | Van Kleef et al. | B01D 3/14 196/100 |
| 3,208,514 A * | 9/1965 | Dew | E21B 43/243 166/261 |
| 3,237,376 A | 3/1966 | Bauer | |
| 3,396,101 A | 8/1968 | Broughton | |
| 3,544,453 A * | 12/1970 | Thompson | B01D 11/0488 208/321 |
| 5,399,244 A * | 3/1995 | Gentry | B01D 3/40 203/23 |
| 8,431,758 B2 | 4/2013 | Frey et al. | |
| 8,609,922 B2 | 12/2013 | Werba et al. | |
| 8,821,696 B2 | 9/2014 | Noe et al. | |

(Continued)

OTHER PUBLICATIONS

Tututi-Avila, Salvador et al., Analysis of Multi-Loop Control Structures of Dividing-Wall Distillation Columns Using a Fundamental Model, Feb. 24, 2014, Processes, p. 183-187.*

(Continued)

*Primary Examiner* — Cabrena Holecek

(57) ABSTRACT

Processes for the recovery of aromatic hydrocarbons from one or more vent gas streams associated with an aromatic complex. The vapor streams are passed to an absorption zone in which an aromatic-selective solvent absorbs the aromatics. The aromatic-selective solvent can be processed along with other solvent extraction streams within the aromatic complex. The absorption zone may be a portion of an existing vessel or column, such as an extractive distillation column or a stabilizer.

15 Claims, 4 Drawing Sheets

(56) References Cited

U.S. PATENT DOCUMENTS

2010/0300830 A1* 12/2010 Noe .................. C10G 21/00
                                                    196/98
2014/0248193 A1    9/2014 Corradi et al.

OTHER PUBLICATIONS

Search Report dated Jul. 14, 2016 for corresponding PCT Appln. No. PCT/US2015/064376.
U.S. Appl. No. 14/195,000, filed Mar. 3, 2014, Corradi et al.

* cited by examiner

PROCESSES FOR THE RECOVERY OF AROMATIC HYDROCARBONS FROM VAPOR GAS STREAMS

FIELD OF THE INVENTION

This invention relates generally to processes for recovering aromatic hydrocarbons from a vapor stream and more particularly to processes for the recovery of aromatic hydrocarbons from a vapor stream with an aromatic selective solvent.

BACKGROUND OF THE INVENTION

Aromatic intermediates such as benzene, toluene and xylenes ("BTX") may be obtained from petroleum naphtha, using a combination of processes to form and recover the desired aromatics. Catalytic reforming generally is the heart of an aromatics complex, producing a mixture of principally aromatics and paraffinic hydrocarbons to be processed further by some combination of aromatics extraction, dealkylation, transalkylation, disproportionation, adsorption or crystallization, isomerization and fractionation. The various steps were combined to address the issues of achieving high aromatics purity, balancing the product slate in favor of the relatively higher demand for benzene and xylenes, and dealing with the ethylbenzene contained in the mixed xylenes stream. Substantial improvements have been effected in individual processes contained in such aromatics complexes, particularly in catalytic reforming efficiency for aromatics production and in isomerization for conversion of $C_8$ aromatics. Exemplary aromatics complexes are described in, for example, U.S. Pat. Nos. 8,609,922 and 8,431,758.

A common feature of many BTX aromatic complexes is one or more vent gas (or off-gas) streams. The vent gas streams comprise significant amounts of desirable aromatics components. The vent gas streams may comprise a vapor stream from a cold separator vessel, a vapor stream from a vent drum for a fractionation column, a vapor stream from a separator, or a vapor stream from a receiver associated with a stripper column. For example, many aromatics complexes include a stripper column for a transalkylation effluent. The overhead vapor from the column comprises a mixture of light ends ($C_3$-hydrocarbons) and some aromatic hydrocarbons.

The above sources of waste gas can be split into categories: continuous and intermittent. The continuous sources comprise the receivers and vent drums while the intermittent sources include the separators and cold separators. The continuous sources constantly produce a vapor stream, while the production of a vapor stream from the intermittent sources depends on a number of factors, including processing conditions and feed quality.

Aromatic hydrocarbons that are recovered from the waste gas can be converted to benzene or paraxylene. If the aromatic hydrocarbons are left in the waste gas, the aromatic hydrocarbons will be used as fuel gas for heating. The benzene and para-xylene can be more than twice as valuable as the fuel gas. Therefore, it would be more desirable to recover the aromatics from these vapor streams instead of using the aromatics as less valuable fuel gas.

In order to recover the aromatics from the vapor streams associated with the continuous sources discussed above, the pressure on the columns is increased or the vent gas is compressed. The vent gas stream is then chilled in order to recover as much as benzene and heavier aromatic hydrocarbons as possible. This recovery process is typically performed at the highest off-gas system pressure.

However, a drawback of these is the necessary increased energy consumption required to compress vapor streams or refrigerant streams. Additionally, further energy may be wasted if the reboilers of the associated fractionation columns are now too hot to be heat integrated with another process stream. Therefore, since refiners are constantly seeking to improve yields and recovery, the recovery of the aromatic hydrocarbons from the vent gas is desired, but the energy consumption and loss are a drawback for the recovery.

With respect to the intermittent sources, it is believed that very little is done to attempt to recover the aromatic hydrocarbons from these sources of vent gas.

Accordingly, there remains a need for an effective and efficient process for recovering the aromatic hydrocarbons from a vapor stream.

It would be desirable to provide a process that also effectively and efficiently allows for the aromatic hydrocarbons to be recovered from the vent gas from an intermittent source.

SUMMARY OF THE INVENTION

One or more process have been invented for the recovery of aromatic hydrocarbons from a vapor stream which requires less energy to separate the aromatics from the vapor streams. Additionally, such processes may be economically used with the vent gas associated with an intermittent source.

Therefore, in a first aspect of the present invention, the invention may be broadly characterized as a process for recovering aromatic hydrocarbons from a vapor stream by: passing a vapor stream to an absorption zone, the vapor stream comprising light ends and aromatic hydrocarbons; passing a solvent into the absorption zone, wherein the solvent is an aromatic selective solvent for absorbing aromatic hydrocarbons; and, separating the vapor stream into at least an aromatic lean vapor stream and a solvent stream rich in aromatic hydrocarbons.

In one or more embodiments, the aromatic selective solvent is selected from the group consisting of: 1,1-dioxide tetrahydrothiofuran or tetrahydrothiophene 1,1-dioxide; 2-sulfolene, 3-sulfolene, 2-methylsulfolane, 2-4-dimethyl sulfolane, methyl-2-sulfonylether, N-aryl-3-sulfonylamine, ethyl-3-sulfonyl sulfide, 2-sulfonylacetate, diethyleneglycol, polyethyleneglycol, dipropyleneglycol, polypropyleneglycol, dimethylsulfoxide, N-methylpyrrolidone, glycolamine, glycols, and glycol ethers including polyethyleneglycolether, N-methyl-2-pyrrolidone, N-formyl morpholine; an ionic liquid; and, combinations thereof.

In or more embodiments, the absorption zone comprises a vessel having at least one separation section.

In some embodiments, the process further comprises passing a liquid feed comprising $C_6$-hydrocarbons and aromatic hydrocarbons to the vessel. It is contemplated that the vessel comprises two separation sections and the two separation sections are separated by an accumulator tray. It is further contemplated that the process includes recovering the solvent stream rich in aromatic hydrocarbons from the vessel on a top of the accumulator tray.

In various embodiments, the process includes separating the aromatic lean vapor stream into a liquid hydrocarbon stream and a fuel gas stream. It is contemplated that the process also includes passing the liquid hydrocarbon stream to the vessel of the absorption zone.

In at least one embodiment, the process includes passing the solvent stream rich in aromatic hydrocarbons to an aromatics extraction unit to separate the solvent and the aromatic hydrocarbons.

In some embodiments, the absorption zone comprises a vessel and the process further includes passing a liquid feed comprising $C_6$-hydrocarbons and aromatic hydrocarbons to the vessel. It is contemplated that the vessel is a split-shell vessel having a vertical baffle dividing the vessel. It is further contemplated that the vertical baffle of the split-shell vessel is disposed in an upper portion of the vessel and the upper portion is divided into two portions and the top of the vessel is undivided. The process may further include separating the aromatic lean vapor stream into a liquid hydrocarbon stream and a fuel gas stream. It is contemplated that the process also includes passing the liquid hydrocarbon stream to the vessel of the absorption zone.

In one or more embodiments, the process includes stabilizing a raffinate stream from an aromatics extraction unit in a stabilization zone. It is contemplated that the stabilization zone comprises a split-shell stabilizer column. It is further contemplated that the process includes passing a liquid hydrocarbon stream to the stabilization column, wherein the liquid hydrocarbon stream includes aromatic hydrocarbons. The process may also include recovering a benzene rich stream from the stabilization column and recovering a stabilized raffinate stream from the stabilization column.

In a second aspect of the present invention, the invention may be broadly characterized as a process for recovering aromatic hydrocarbons from a vapor stream by: passing a vapor stream to an absorption zone, the vapor stream comprising light ends and aromatic hydrocarbons, and the absorption zone comprising a vessel with a separation section; passing an aromatic selective solvent into the vessel of the absorption zone above the separation section; separating the vapor stream into at least an aromatic lean vapor stream and a solvent stream rich in aromatic hydrocarbons; and, passing the solvent stream rich in aromatic hydrocarbons to an aromatics extraction unit to separate the solvent and the aromatic hydrocarbons.

In a third aspect of the present invention, the invention may be broadly characterized as a process for recovering aromatic hydrocarbons from a vapor stream by: passing a vapor stream to an absorption zone, the vapor stream comprising light ends and aromatic hydrocarbons, and the absorption zone comprising a vessel with a first separation section, a second separation section disposed below the first separation section, and an accumulation tray separating the first separation section from the second separation section; passing an aromatic selective solvent into the vessel of the absorption zone above the second separation section; separating the vapor stream into at least an aromatic lean vapor stream and a solvent stream rich in aromatic hydrocarbons; stabilizing a liquid stream including aromatics in the vessel of the absorption zone; and, passing the solvent stream rich in aromatic hydrocarbons to an aromatics extraction unit to separate the solvent and the aromatic hydrocarbons.

Additional aspects, embodiments, and details of the invention are set forth in the following detailed description of the invention.

DETAILED DESCRIPTION OF THE DRAWINGS

In the drawings of the present invention, one or more embodiments are shown in which like numerals denote like elements, and in which.

DETAILED DESCRIPTION OF THE INVENTION

As mentioned above, various processes for the recovery of aromatic hydrocarbons from a vapor stream have been invented. The processes generally comprise utilizing an aromatic selective solvent to separate the aromatic hydrocarbons from the vapor stream. The solvent stream can be processed along with other streams in an aromatic complex to separate the aromatic hydrocarbons and the solvent. In addition to the energy savings, a refiner will be able to increase the recovery of the aromatic hydrocarbons.

With these general principles in the mind, one or more embodiments of the present invention will now be described with the understanding that the described embodiments are merely exemplary and are not intended to be limiting.

Figure 1:
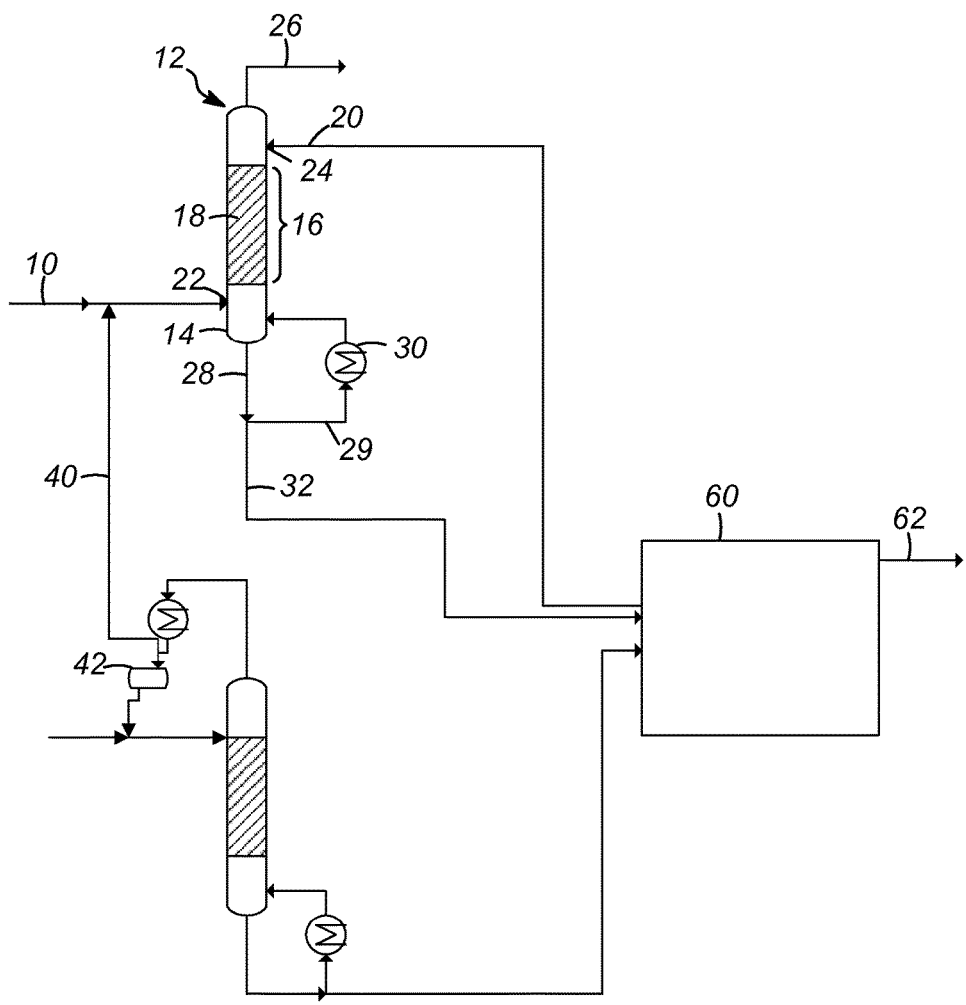
FIG. 1 shows a process flow diagram of one or more embodiments of the present invention.

As shown in FIG. 1, aromatic hydrocarbons are recovered from a vapor stream 10 that typically comprises a mixture of light ends ($C_3$-hydrocarbons) and aromatic hydrocarbons. As appearing herein, the terms "aromatic," "aromatic hydrocarbon," and the like are utilized to denote a hydrocarbon containing one or more rings of unsaturated cyclic carbon radicals where one or more of the carbon radicals can be replaced by one or more non-carbon radicals.

In preferred embodiments, the vapor stream 10 is a vent gas stream from an aromatics complex. Additionally, it is contemplated that the vapor stream 10 comprises a combined stream, including sources that are continuously producing the vapor stream and sources that are intermittently producing the vapor stream. For example, a continuous source for the vapor stream may comprise a stripper net overhead vapor from a transalkylation unit or a stripper net overhead vapor from an aromatic isomerization unit. An intermittent source for the vapor stream may comprise a transalkylation reactor effluent separator net vapor or an aromatic isomerization reactor effluent separator net vapor. However, other vapor streams having mixtures of light ends and aromatics can likewise be utilized in accordance with the present invention, for example a vapor stream 40 from a stabilizer overhead condenser 42 (discussed in more detail below in regards to FIG. 2).

Returning to FIG. 1, in order to recover the more valuable aromatic hydrocarbons, the vapor stream 10 is passed to an absorption zone 12. The absorption zone 12 comprises a vessel 14, preferably having at least one separation section 16 comprised of trays 18, packing (such as structured packing), or the like. As can be seen, the vapor stream 10 is passed into the vessel 14 below the separation section 16 via a vapor stream inlet 22 disposed proximate a bottom of the vessel 14 and below the separation section 16. The sources of the vapor stream 10 can be combined before entering the vessel 14, as is shown, or may each enter the vessel 14 individually.

An aromatic-selective solvent 20 is also passed into the vessel 14 of the absorption zone 12. A solvent inlet 24 for the aromatic-selective solvent 20 is disposed proximate a top of the vessel 14 and above the separation section 16. The aromatic-selective solvent 20 may comprises any compound or class of compounds that interacts with the components of vapor stream 10 and which exhibits a greater affinity for the aromatic hydrocarbons. More specifically, the aromatic-selective solvent 20 may comprise a solvent compound including a five-member ring containing one atom of sulfur and four atoms of carbon with two oxygen atoms bonded to the sulfur atom of the ring. In a preferred embodiment, the aromatic-selective solvent 20 comprises 1,1-dioxide tetrahydrothiofuran or tetrahydrothiophene 1,1-dioxide (also known as "tetramethylene sulfone" and commonly referred to as "sulfolane"). A non-exhaustive list of additional exemplary solvent compounds that may be included in solvent stream 20 includes 2-sulfolene, 3-sulfolene, 2-methylsulfolane, 2-4-dimethyl sulfolane, methyl-2-sulfonylether, N-aryl-3-sulfonylamine, ethyl-3-sulfonyl sulfide, 2-sulfonylacetate, diethyleneglycol, polyethyleneglycol, dipropyleneglycol, polypropyleneglycol, dimethylsulfoxide, N-methylpyrrolidone, glycol-amine, glycols, and glycol ethers including polyethyleneglycolether, N-methyl-2-pyrrolidone, N-formyl morpholine, an ionic liquid, or combinations of any of the foregoing.

Moreover, since the absorption zone 12 typically comprises a portion of a larger aromatics complex, it is contemplated that the aromatic-selective solvent 20 is the same solvent that is used elsewhere in the aromatics complex. Not only will such a configuration minimize additional solvent, as described in detail below, such a configuration will also allow for the separation and recovery of aromatics from the aromatic-selective solvent 20 to be fully integrated with the existing aromatic complex. It is believed that the rate of solvent injection will be between about 1 and 20 mol solvent/mol aromatics.

Aromatic hydrocarbon components from the vapor stream 10 and some of the non-aromatic components are absorbed into the liquid phase of the aromatic-selective solvent 20.

An aromatic vapor lean stream 26 may be recovered from an overhead of the vessel 14 and processed further as fuel gas. Typically, the further processing of the fuel gas would require a chiller. However, with the removal of the aromatic hydrocarbons from the vapor stream 10, it is believed that a chiller is not necessary.

A solvent stream rich in aromatic hydrocarbons 28 may also be recovered from the vessel 14. A portion 29 of the solvent stream rich in aromatic hydrocarbons 28 may be passed to a heat exchanger 30 to be heated and then passed back to the vessel 14 to provide an appropriate temperature to the vessel 14 for the separation of the light ends from the solvent/aromatics hydrocarbons, which may be between 100° and 200° C. (210° and 390° F.). The reheating of the portion 29 preferably produces a sufficient amount of vapor to minimize the concentration of light hydrocarbon components ($C_3$-hydrocarbons) in a net solvent stream rich in aromatic hydrocarbons 32 from the bottom of the vessel 14 in the absorption zone 12.

The net solvent stream rich in aromatic hydrocarbons 32 may be passed to an aromatic extraction unit 60 to provide an aromatic product stream 62. The aromatic extraction unit 60 may comprise an extractive distillation zone having an extractive distillation column and a recovery column. Such aromatic extraction units 60 are known in the art. See, U.S. Pat. No. 8,608,912. The aromatic product stream 62 can be separated and processed as desired.

Figure 2:
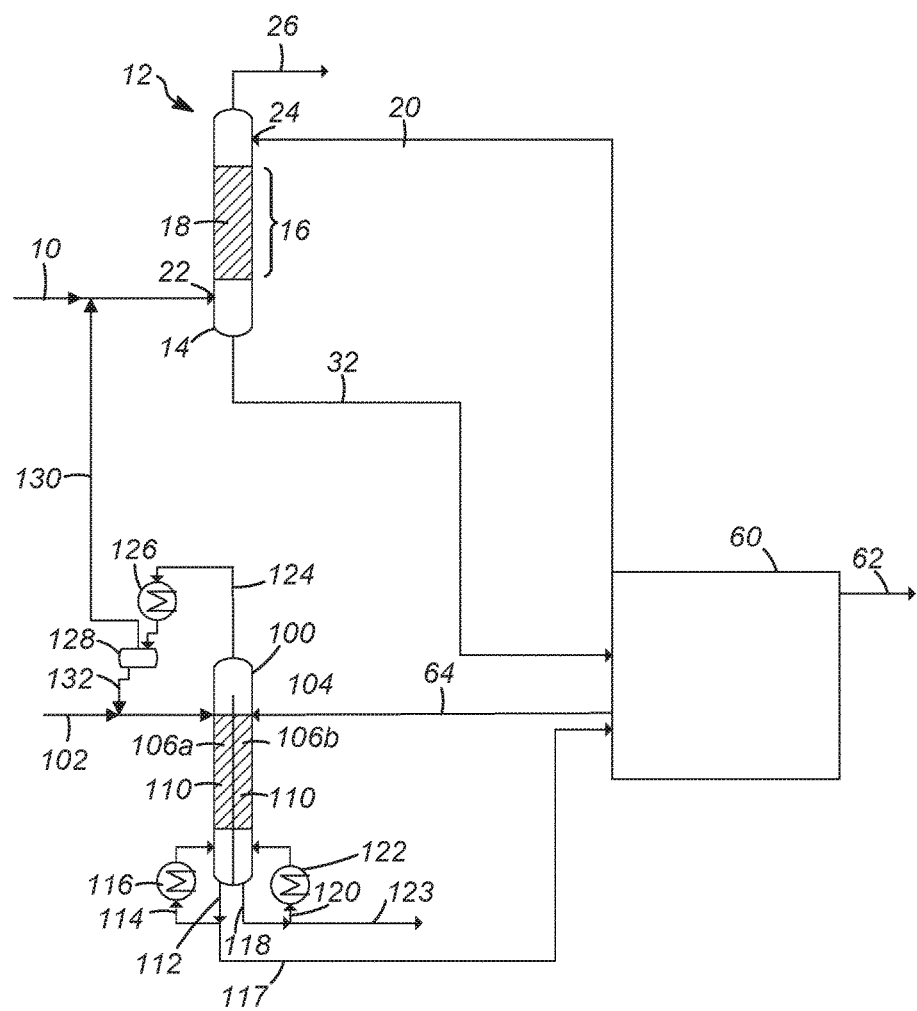
FIG. 2 shows another process flow diagram of one or more embodiments of the present invention.

Turning to FIG. 2, another process is shown which is similar to the process in FIG. 1 except that the reboiler 30 for the absorption zone 12 is not included. Without the reboiler, any light hydrocarbon components ($C_3$-hydrocarbons) that are absorbed in the net solvent stream rich in aromatic hydrocarbons 32 are allowed to pass through to the aromatic extraction unit 60, where they will be condensed and combined with a raffinate stream 64 from the aromatic extraction unit 60. This could increase the vapor pressure of the raffinate stream 64 above its allowed limit. Accordingly, it is contemplated that the raffinate stream 64 is processed in a stabilizing column 100.

In a typical aromatics complex, there are several unstabilized or "wild" light aromatics streams that are collected and sent to a stabilizer column to remove light hydrocarbons. As shown in FIG. 2, a stabilization column 100 may receive a liquid stream 102 comprising $C_5$-hydrocarbons and aromatics. It will be appreciated that other streams may be used in accordance with the present invention.

As can be seen in FIG. 2, a vertical baffle 104 is used to separate the column into two stabilization sections 106a, 106b. The vertical baffle 104 extends from the bottom of the stabilization column 100 towards, but not completely to, the top of the stabilization column 100. In this manner, the two stabilization sections 106a, 106b will share an overhead section 108. Each stabilization section 106a, 106b may include a section with trays 110, packing, or the like.

The first stabilization section 106a will receive the liquid stream 102, preferably above the trays 110. The liquid will flow downward and pass through the trays 110 to the bottom of the stabilization column 100. An aromatic rich stabilized stream 112 is withdrawn from the bottom of stabilization column 100. A portion 114 of the aromatic rich stabilized stream 112 liquid is circulated through a heat exchanger 116, which reheats the liquid, vaporizing a portion of it. Enough vapor will be produced to minimize the concentration of light hydrocarbon components in the net liquid stream 117 from the bottom of the first stabilization section 106a of the stabilization column 100. The aromatic rich stabilized stream 117 from this stabilization section 106a from the stabilization column 100 may be sent to the aromatics extraction unit 60 (for example, to an extractive distillation column).

The second stabilization section 106b will receive the raffinate stream 64 from the aromatic extraction zone 60. It is preferred that the raffinate stream 64 pass into the stabilization column 100 above the trays 110. The liquid will flow downward and pass through the trays 110 to the bottom of the stabilization column 100. A stabilized raffinate stream 118 may be withdrawn from the stabilization column 100 with a portion 120 of this liquid being circulated through a heat exchanger 122, which reheats the liquid vaporizing a portion of it to produce enough vapor to minimize the concentration of light hydrocarbon components in a net stabilized raffinate stream 123 from the bottom of the second stabilization section 106b of the stabilization column 100. The net liquid 123 from this stabilization section 106b of the stabilization column 100 is sent to storage, gasoline blending, or another process unit.

Returning to the stabilization column 100, vapor exiting the top of trays 110 from both stabilization section 106a, 106b are combined in the overhead section 108 of the stabilization column 100. A combined overhead vapor stream 124 may be passed to a condenser 126 and a receiver 128 to separate into a vapor stream 130 and a liquid stream 132. The liquid stream 132 may be combined with the liquid stream 102 passed into the stabilization column 100. The vapor stream 130 from the receiver 128 may be combined with the vapor stream 10 being passed into the absorption zone 12. The remaining portions of this embodiment are similar to the one shown in FIG. 1.

Figure 3:
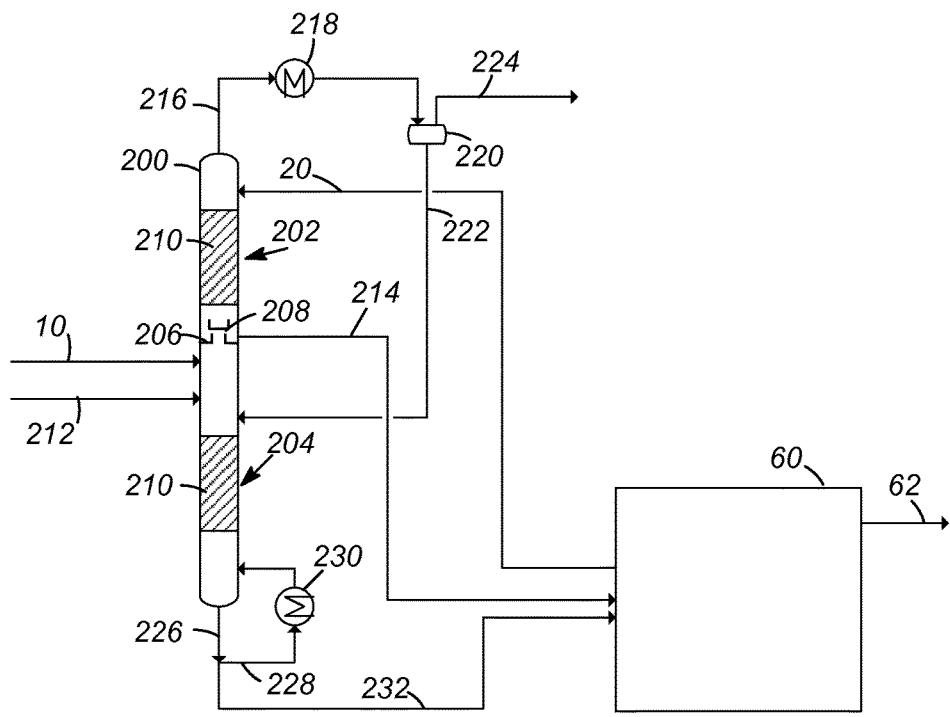
FIG. 3 shows an alternative process flow diagram of one or more embodiments of the present invention; and, FIG. 4 shows still another process flow diagram of one or more embodiments of the present invention.

Turning to FIG. 3, in some embodiments of the present invention, the absorption zone for recovering the aromatic hydrocarbons in a vapor stream may be combined into a single vessel with an existing column/vessel such as a stabilizer or stripping column.

As shown in FIG. 3, a column 200 comprises two zones: an upper absorption zone 202; and a lower stripping zone 204. The two zones 202, 204 are separated by an accumulator tray 206, which collects all of the liquid from the bottom of the absorption zone 202. All vapor from the top of the stripping zone 204 passes through a chimney 208 located in the accumulator tray 206 and proceeds to the bottom of the absorption zone 202. Both the absorption zone 202 and the stripping zone 204 are comprised of trays 210, packing, or the like.

The vapor stream 10 comprising light ends and aromatic hydrocarbons is passed into the column 200. The vapor stream 10 will preferably enter the column 200 below the trays 210 in the upper absorption zone 202 and, below the accumulator tray 206 as well.

A liquid stream 212 comprising a mixture of $C_6$-hydrocarbons and aromatic hydrocarbons is introduced into the column 200, preferably above the trays 210 in the lower stripping section 204. Alternatively, although not shown the liquid stream 212 may be passed into the column 200 within the trays 210. Additionally, multiple liquid streams 212 may be combined together, or separately passed into the column 200.

The solvent stream 20 comprising an aromatic selective solvent is also passed into the column 200, above the trays 210 in the upper absorption zone 202. The aromatic selective solvent will flow downward in the column 200 and through the trays 210 in the upper absorption zone 202. Aromatic hydrocarbon components and some of the non-aromatic components from the vapors in the upper absorption zone 202 will be absorbed into the solvent.

A hydrocarbon-rich solvent stream 214 is collected by the accumulator tray 206 and may be recovered from the bottom of the absorption section 202. The hydrocarbon-rich solvent stream 214 may be passed to an aromatics extraction unit 60 having, for example, an extractive distillation column (not shown).

A vapor stream 216 from the absorption section 202 may be recovered from the column 200, condensed in a condenser 218, and separated in an overhead receiver 220. A condensed liquid stream 222 may be passed back to the column between the accumulator tray 206 and the trays 210 of the stripping zone 204. A vapor stream 224 can be utilized as fuel gas. Unlike the previous flow schemes, the vapor stream 224 will contain a significant amount of $C_5$ and $C_6$ non-aromatic hydrocarbons.

A liquid stream 226 from the stripping zone 204 of the column 200 can be recovered below the trays 210 in the stripping zone 204. A portion 228 of this liquid is circulated through a heat exchanger 230, which reheats the liquid, vaporizing enough of the liquid so that sufficient vapor is produced to minimize the concentration of light hydrocarbon components in the net liquid stream 232 from the stripping zone 204. The net liquid stream 232 from the column may be passed to the aromatics extraction unit 60, albeit separately from the hydrocarbon-rich solvent stream 214 discussed above.

Figure 4:
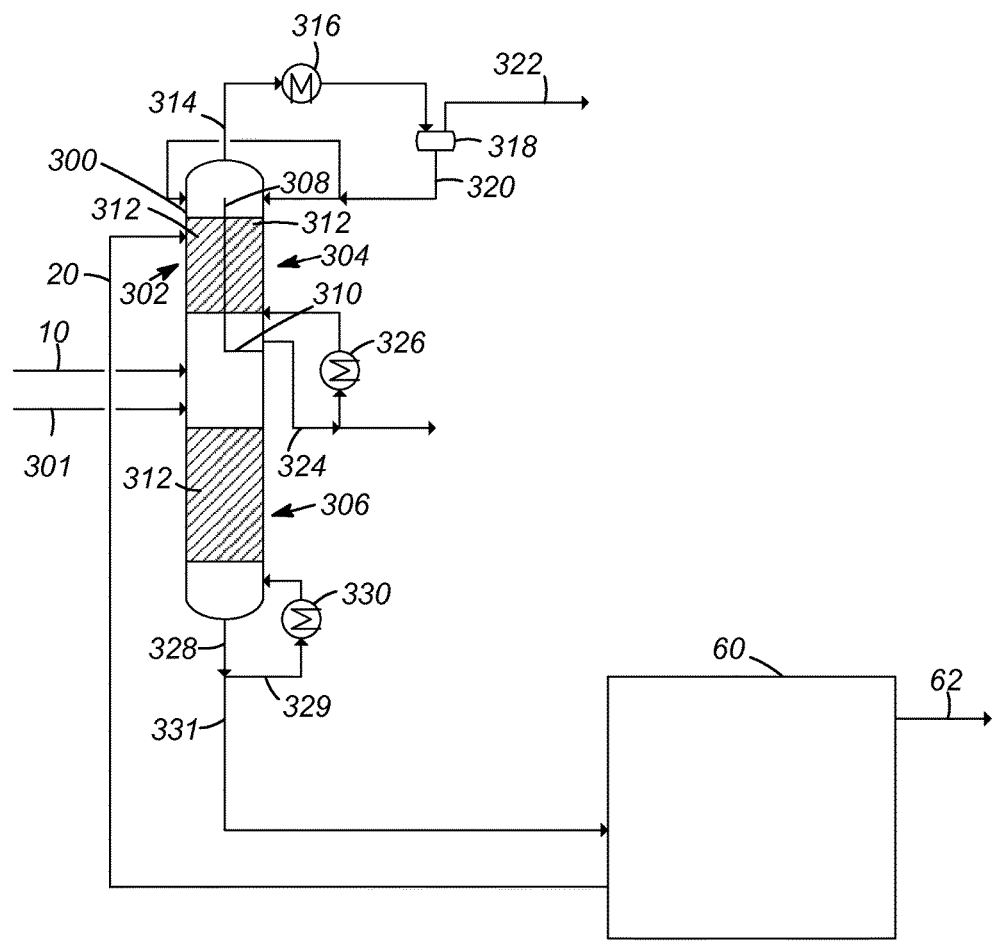

Turning to FIG. 4, another embodiment is shown in which the absorption zone for recovering aromatics from a vapor stream is combined with another vessel or column, in this case with an extractive distillation column and a stabilization column.

As shown in FIG. 4, a column 300 comprises three zones: an absorption zone 302; an upper stripping zone 304; and a lower stripping zone 306. The absorption zone 302 and the upper stripping zone 304 are generally parallel and separated by a vertical baffle 308, such that an upper portion of each zone is in open communication. An accumulator tray 310 is disposed at the bottom of the upper stripping zone 304 which collects all of the liquid from the upper stripping zone 304. In this manner, all of the vapor from the lower stripping zone 306 will pass into the absorption zone 302. Each of the three zones includes trays 312, packing or the like.

The vapor stream 10 comprising light ends and aromatic hydrocarbons is passed to the column 300, preferably between the lower stripping zone 306 and the absorption zone 302.

A liquid feed 301 comprising a mixture of $C_6$-hydrocarbons and aromatic hydrocarbons is introduced into the column 300, preferably between the lower stripping zone 306 and the adsorption zone 302. Alternatively, it is contemplated that the liquid feed 301 is passed into the trays 312 of the lower stripping zone 306.

The solvent stream 20 comprising an aromatic-selective solvent is also passed into the column 300 into the trays 310 in the absorption zone 302. The solvent will flow downward in the column 300 and aromatic hydrocarbon components and some of the non-aromatic components from the rising vapor in the column will be absorbed into the solvent.

An overhead vapor stream 314 from the column 300, may be condensed in a condenser 316, and separated in an overhead receiver 318. A condensed liquid stream 320 may be divided and sent back to the column 300 above the trays 312 of the upper stripping zone 304 and the absorption zone 302. Similar to the embodiment in FIG. 3, a vapor stream 322 from the column will contain a significant amount of $C_5$ and $C_6$ non-aromatic hydrocarbons.

Liquid from the upper stripping zone 304 will collect on the accumulator tray 310 and can be withdrawn in a raffinate stream 324. A portion of the raffinate stream 324 may be circulated through a heat exchanger 326, which reheats the liquid and vaporizes a portion of the liquid so that enough vapor is produced to minimize the concentration of light hydrocarbon components in the net liquid from the upper stripping zone 304. The remaining portion of the raffinate stream 324 may be sent to storage, gasoline blending, or another process unit.

A hydrocarbon rich solvent stream 328 can be recovered from the bottom of the column 300. A portion 329 of the hydrocarbon rich solvent stream 328 may be passed to a heat exchanger 330, which reheats the liquid, vaporizing the liquid so that enough vapor is produced to strip the non-aromatic hydrocarbon components from a net liquid 331 from the bottom of the column 300. The net liquid 331, which is a hydrocarbon rich solvent stream, may be passed to the aromatics extraction unit 60. One additional advantage provided in this embodiment is that an extractive distillation column within aromatics extraction unit 60 may now be smaller because this flow scheme decouples the processing of a fresh light aromatics stream and a recycle light aromatics stream. This will allow a smaller column, as less feed will be passed directly to the extractive distillation column.

In the various processes, the recovery of aromatics from various waste vapor streams will increase the recovery of the aromatics with less energy input and will allow for recovery from waste vapor streams that may be intermittent. In a theoretical modeling, the capital costs and operating expenses associated with implementing one or more processes are believed to be offset within two or three years by the increased recovery of the more valuable aromatic hydrocarbons.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for recovering aromatic hydrocarbons from a vapor stream, the process comprising:
   passing a vapor stream to an absorption zone comprising a vessel, the vapor stream comprising C3-hydrocarbons and aromatic hydrocarbons;
   passing a solvent into the vessel at a first inlet, the first inlet disposed above a second inlet, the second inlet receiving the vapor stream, wherein the solvent is an aromatic selective solvent for absorbing aromatic hydrocarbons;
   separating the vapor stream into at least an aromatic lean vapor stream and a solvent stream rich in aromatic hydrocarbons; and,
   passing the solvent stream rich in aromatic hydrocarbons to an aromatics extraction unit configured to separate the solvent and the aromatic hydrocarbons, wherein the aromatic extraction unit includes an extractive distillation column, wherein the aromatic extraction unit further provides a raffinate stream, and the process further comprising stabilizing the raffinate stream from the aromatics extraction unit in a stabilization zone, wherein the stabilization zone comprises a split-shell stabilizer column.

2. The process of claim 1 wherein the aromatic selective solvent is selected from the group consisting of: 1,1-dioxide tetrahydrothiofuran or tetrahydrothiophene 1,1-dioxide; 2-sulfolene, 3-sulfolene, 2-methylsulfolane, 2-4-dimethyl sulfolane; or combinations thereof.

3. The process of claim 1 further comprising:
   wherein the vessel of the absorption zone comprises at least one separation section.

4. The process of claim 3 further comprising:
   passing a liquid feed comprising C6-hydrocarbons and aromatic hydrocarbons to the vessel.

5. The process of claim 4 wherein the vessel comprises two separation sections and the two separation sections are separated by an accumulator tray.

6. The process of claim 5 further comprising:
   recovering the solvent stream rich in aromatic hydrocarbons from the vessel on a top of the accumulator tray.

7. The process of claim 3 further comprising:
   separating the aromatic lean vapor stream into a liquid hydrocarbon stream and a fuel gas stream.

8. The process of claim 7 further comprising:
   passing the liquid hydrocarbon stream to the vessel of the absorption zone.

9. The process of claim 1 further comprising:
   passing a liquid feed comprising C6-hydrocarbons and aromatic hydrocarbons to the vessel, wherein the liquid feed is passed into the vessel below the second inlet for the vapor stream.

10. The process of claim 9 wherein the vessel comprises:
    a split-shell vessel having a vertical baffle dividing the vessel.

11. The process of claim 10 wherein the vertical baffle of the split-shell vessel is disposed in an upper portion of the vessel and the upper portion is divided into two portions, and the top of the vessel being undivided.

12. The process of claim 11 further comprising:
    separating the aromatic lean vapor stream into a liquid hydrocarbon stream and a fuel gas stream.

13. The process of claim 12 further comprising:
    passing the liquid hydrocarbon stream to the vessel of the absorption zone.

14. The process of claim 1 further comprising:
    passing a liquid hydrocarbon stream to the split-shell stabilizer column, wherein the liquid hydrocarbon stream includes aromatic hydrocarbons.

15. The process of claim 14 further comprising:
    recovering a benzene rich stream from the split-shell stabilizer column; and,
    recovering a stabilized raffinate stream from the split-shell stabilizer column.

* * * * *